US010371693B2

(12) United States Patent
Lee et al.

(10) Patent No.: US 10,371,693 B2
(45) Date of Patent: Aug. 6, 2019

(54) PORTABLE BLOOD GLUCOSE MEASUREMENT DEVICE

(71) Applicant: I-SENS, INC., Seoul (KR)

(72) Inventors: Jin Won Lee, Seoul (KR); Chang Woo Ryu, Seoul (KR); Geun Sig Cha, Seoul (KR); Hak hyun Nam, Seoul (KR)

(73) Assignee: I-SENS, INC., Seoul (KR)

( * ) Notice: Subject to any disclaimer, the term of this patent is extended or adjusted under 35 U.S.C. 154(b) by 249 days.

(21) Appl. No.: 15/313,258

(22) PCT Filed: May 22, 2015

(86) PCT No.: PCT/KR2015/005207
§ 371 (c)(1),
(2) Date: Nov. 22, 2016

(87) PCT Pub. No.: WO2015/178737
PCT Pub. Date: Nov. 26, 2015

(65) Prior Publication Data
US 2017/0138929 A1    May 18, 2017

(30) Foreign Application Priority Data
May 22, 2014    (KR) .................. 10-2014-0061595

(51) Int. Cl.
*G01N 25/00*        (2006.01)
*G01N 33/49*        (2006.01)
(Continued)

(52) U.S. Cl.
CPC ............. *G01N 33/49* (2013.01); *A61B 5/145* (2013.01); *A61B 5/14532* (2013.01); *G01J 5/10* (2013.01);
(Continued)

(58) Field of Classification Search
None
See application file for complete search history.

(56) References Cited

U.S. PATENT DOCUMENTS 2,941,869 A *  6/1960  Brown .................. G01N 33/49
                                                      422/401
7,494,816 B2 *  2/2009  Burke ................. G01N 27/3274
                                                      422/82.01
(Continued)

FOREIGN PATENT DOCUMENTS

JP    2007-010317 A    1/2007
JP    2011-064597 A    3/2011
(Continued)

OTHER PUBLICATIONS

EPO translation of JP2007010317.*

*Primary Examiner* — Lisa M Caputo
*Assistant Examiner* — Nasir U. Ahmed
(74) *Attorney, Agent, or Firm* — Ladas & Parry, LLP

(57) ABSTRACT

A portable blood glucose measurement device is provided. The device includes, in an externally exposed way, a temperature measurement medium of which the temperature quickly changes according to outside temperature changes provided on one side surface of a case. The device further includes an infrared temperature sensor. The device measures the temperature of the temperature measurement medium with the infrared temperature sensor in a noncontact manner, and calculates a blood glucose measurement result by considering the measured temperature so as to accurately reflect the outside temperature of an actual blood glucose measuring environment. The temperature measurement medium can be configured to sensitively respond to the outside temperature independently from the case such that the temperature of the temperature measurement medium, in accordance with the change in outside temperature, quickly and accurately changes so as to measure the temperature in a more accurate manner.

16 Claims, 4 Drawing Sheets

(a)

(b)

(51) Int. Cl.
 *A61B 5/145* (2006.01)
 *G01N 33/66* (2006.01)
 *G01N 27/327* (2006.01)
 *G01J 5/10* (2006.01)
(52) U.S. Cl.
 CPC ......... *G01N 25/00* (2013.01); *G01N 27/3274* (2013.01); *G01N 33/66* (2013.01)

(56) References Cited

U.S. PATENT DOCUMENTS

| | | | | |
|---|---|---|---|---|
| 2010/0130838 | A1* | 5/2010 | Kermani | G01J 5/04 |
| | | | | 600/310 |
| 2010/0307916 | A1* | 12/2010 | Ramey | A61B 5/14532 |
| | | | | 204/402 |
| 2010/0309947 | A1* | 12/2010 | Parasnis | A61B 5/14532 |
| | | | | 374/1 |
| 2012/0179017 | A1* | 7/2012 | Satou | A61B 5/14532 |
| | | | | 600/365 |

FOREIGN PATENT DOCUMENTS

| | | |
|---|---|---|
| JP | 2012-506536 A | 3/2012 |
| KR | 10-2010-0032130 A | 3/2010 |
| WO | WO-2010/048303 A1 | 4/2010 |

* cited by examiner (a)

(b)

PORTABLE BLOOD GLUCOSE MEASUREMENT DEVICE

TECHNICAL FIELD

The present disclosure relates to a portable blood glucose measuring device. More particularly, the present disclosure relates to a portable blood glucose measuring device including a temperature measuring medium disposed on a surface of a housing thereof, the temperature of the temperature measuring medium changing rapidly, depending on changes in the outside temperature, and an infrared (IR) temperature sensor measuring the temperature of the temperature measuring medium in a contactless manner. The portable blood glucose measuring device can produce a result of measurement of a blood glucose level by considering the measured temperature of the temperature measuring medium, so that the temperature outside of the environment in which blood glucose is actually measured can be accurately reflected, thereby improving the accuracy of the result of measurement of the blood glucose level. The temperature measuring medium is configured to sensitively react to the outside temperature independently of a housing, so that the temperature of the temperature measuring medium rapidly and accurately changes, depending on changes in the outside temperature, thereby being able to more accurately measure the temperature and obtain a more accurate result of measurement of a blood glucose level.

BACKGROUND ART

Diabetes is a chronic disease, common in modern people. In the Republic of Korea, two million or more people, about 5% of the total population, suffer from diabetes.

Diabetes is caused by the pancreas producing an entirely, or relatively, insufficient amount of insulin due to a variety of reasons, such as obesity, stress, poor eating habits, and the like, so that blood glucose levels are absolutely high, instead of being balanced.

Blood contains a certain concentration of glucose, from which the cells of body tissues produce energy.

However, when glucose levels are higher than normal, glucose is not stored appropriately in the liver or muscles, and excessive amounts of glucose remain in the blood. Thus, patients with diabetes have higher glucose levels than other people. Excessive amounts of glucose are discharged in urine without being absorbed by body tissues. Accordingly, the body tissues may malfunction, since the body tissues may fail to have sufficient amounts of glucose that are necessary for normal functioning.

Diabetes has subtle or no subjective symptoms in the early stages of the disease. With the progression of the disease, however, the classic symptoms of diabetes, such as polydipsia, polyphagia, polyuria, weight loss, fatigue, itchy skin, and slow healing of cuts, appear. Prolonged diabetes may cause complications, such as blurred vision, high blood pressure, nephropathy, palsy, periodontal diseases, muscle spasms, neuralgia, and gangrene.

To diagnose and manage diabetes so that complications do not arise, systematic measurement of glucose levels must be carried out in concert with systematic treatment.

For patients with diabetes and people having higher blood glucose levels than normal even though diabetes has not yet occurred, a number of medical device manufacturers provide a range of portable blood glucose measuring devices such that blood glucose levels can be measured at home.

Such a portable blood glucose measuring device is configured to measure the blood glucose level of a blood sample by providing a blood sample to be subjected to a blood glucose level test to a sensor strip, inputting the sensor strip to a housing, and inspecting the blood sample on the input sensor strip using a blood glucose measuring module within the housing. Afterwards, the result of the blood glucose measurement is displayed on a display device disposed on the housing.

Since the blood glucose level of the blood sample varies depending on the temperature at which the blood glucose level is measured, the portable blood glucose measuring device is provided with a temperature sensor for measuring the temperature. The portable blood glucose measuring device is also configured to calculate a blood glucose level by considering the temperature measured using the temperature sensor.

However, in a typical portable blood glucose measuring device of the related art, the temperature sensor is disposed within a housing, so the temperature sensor measures the temperature of the space within the housing. Since the space is isolated from the outer space, the temperature of the space within the housing may change very slowly over time, even in the case in which the temperature of the outer space changes substantially. As a result, the temperature measured by the temperature sensor may fail to properly reflect an actual change in the temperature of the surrounding environment. A blood glucose level calculated by reflecting the temperature measured in this manner may exhibit a result different from an actual blood glucose level.

For example, when a user who has performed an outdoor activity measures a blood glucose level by operating a portable blood glucose measuring device directly after entering an indoor environment, the indoor temperature, i.e. the temperature of the environment in which the blood glucose level is measured, may be a relatively high temperature of, for example, 25° C., but the temperature of the space within the housing of the portable blood glucose measuring device may remain at the outdoor temperature. Thus, the temperature measured using the temperature sensor of the blood glucose measuring device may be a relatively low temperature of, for example, 0° C. In this case, when the blood glucose level is calculated by reflecting the temperature measured using the temperature sensor, the temperature of 0° C. different from the actual temperature of 25° C. of the environment of the measurement may be reflected, whereby the blood glucose level cannot be accurately obtained.

DISCLOSURE

Technical Problem

Accordingly, the present disclosure has been made in consideration of the above problems occurring in the related art, and the present disclosure proposes a portable blood glucose measuring device including a temperature measuring medium disposed on a surface of a housing thereof, the temperature of the temperature measuring medium changing rapidly, depending on changes in the outside temperature, and an infrared (IR) temperature sensor measuring the temperature of the temperature measuring medium in a contactless manner. The portable blood glucose measuring device can produce a result of measurement of a blood glucose level by considering the measured temperature of the temperature measuring medium, so that the temperature outside of the environment in which blood glucose is actually measured can be accurately reflected, thereby improving the accuracy of the result of measurement of the blood glucose level.

Also proposed is a portable blood glucose measuring device including a temperature measuring medium configured to sensitively react to the outside temperature independently of a housing, so that the temperature of the temperature measuring medium rapidly and accurately changes, depending on changes in the outside temperature, thereby being able to more accurately measure the temperature and obtain a more accurate result of measurement of a blood glucose level.

Technical Solution

According to an aspect of the present disclosure, a portable blood glucose measuring device may include: a housing having a strip inlet allowing a sensor strip having a blood sample attached thereto to be input into an inner space of the housing; a printed circuit board disposed within the housing, wherein a blood glucose measuring module able to measure a blood glucose level by inspecting the blood sampled attached to the sensor strip is disposed on the printed circuit board; a temperature measuring medium disposed on the housing to be exposed externally; and an IR temperature sensor disposed within the housing to measure a temperature of the temperature measuring medium in a contactless manner. The blood glucose measuring module produces a result of measurement of the blood glucose level by considering the temperature measured by the IR temperature sensor.

The temperature measuring medium may be made of a material having a relatively small specific heat.

The temperature measuring medium may have the shape of a thin plate.

The temperature measuring medium may include a plurality of embossed protrusions formed on an externally exposed surface.

The housing may have a concave recess depressed in a direction of the inner space thereof. A through-hole may be formed in a bottom of the concave recess, allowing the temperature measuring medium to fitted thereinto. The temperature measuring medium may be fitted into the through-hole, such that the temperature measuring medium does not protrude from a side surface of the housing.

A plurality of fixing protrusions may be formed on an inner circumference of the through-hole to be spaced apart from each other in a radial direction. The temperature measuring medium may be fixedly held by the fixing protrusions.

The fixing protrusions may be formed of an insulating material.

Advantageous Effects

According to the present invention, the temperature measuring medium is disposed on the surface of the housing thereof, the temperature of the temperature measuring medium changing rapidly depending on changes in the outside temperature, and the IR temperature sensor measuring the temperature of the temperature measuring medium in a contactless manner. The portable blood glucose measuring device can produce a result of measurement of a blood glucose level by considering the measured temperature of the temperature measuring medium, so that the temperature outside of the environment in which blood glucose is actually measured can be accurately reflected, thereby improving the accuracy of the result of measurement of the blood glucose level.

In addition, the temperature measuring medium is configured to sensitively react to the outside temperature independently of the housing, so that the temperature of the temperature measuring medium rapidly and accurately changes depending on changes in the outside temperature, thereby being able to more accurately measure the temperature and obtain a more accurate result of measurement of a blood glucose level.

MODE FOR INVENTION

Figure 1:
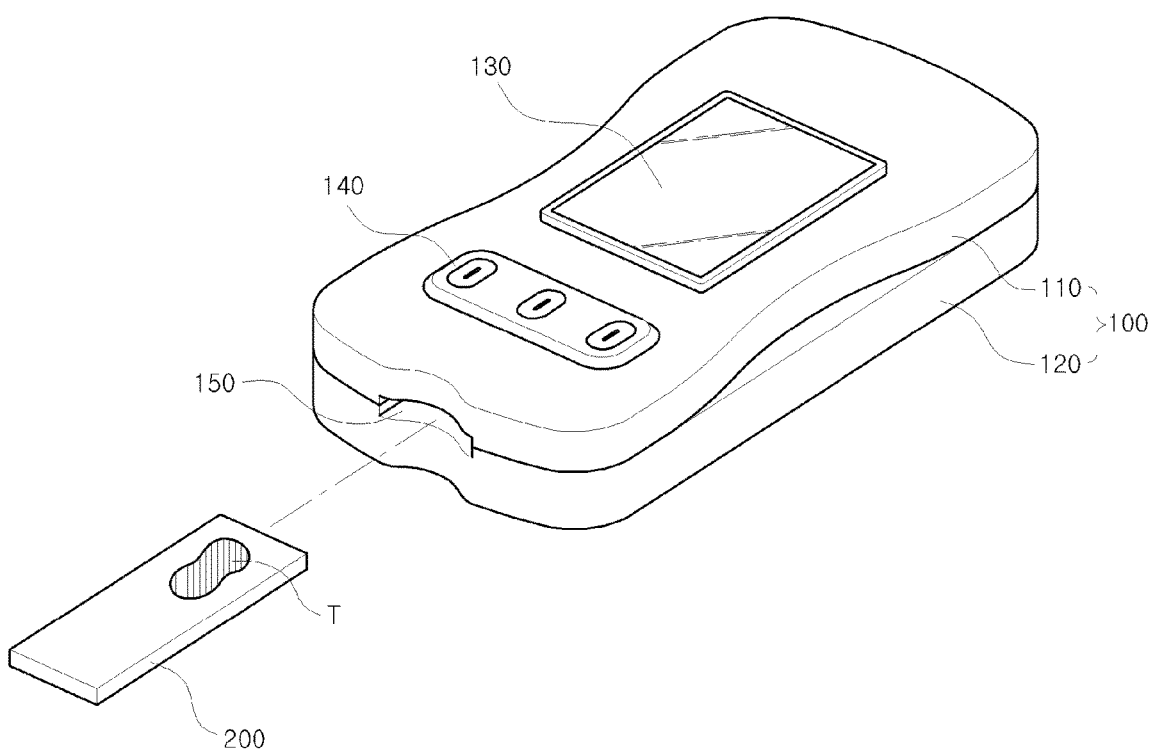
FIG. 1 is a perspective view schematically illustrating the contour of a portable blood glucose measuring device according to an embodiment of the present invention.

Hereinafter, reference will be made to the present invention in detail, examples of which are illustrated in the accompanying drawings and described below. Throughout this document, reference should be made to the drawings, in which the same reference numerals and symbols will be used throughout to designate the same or like components. In the following description, detailed descriptions of known functions and components incorporated herein will be omitted in the case that the subject matter of the present disclosure may be rendered unclear thereby.

Figure 2:
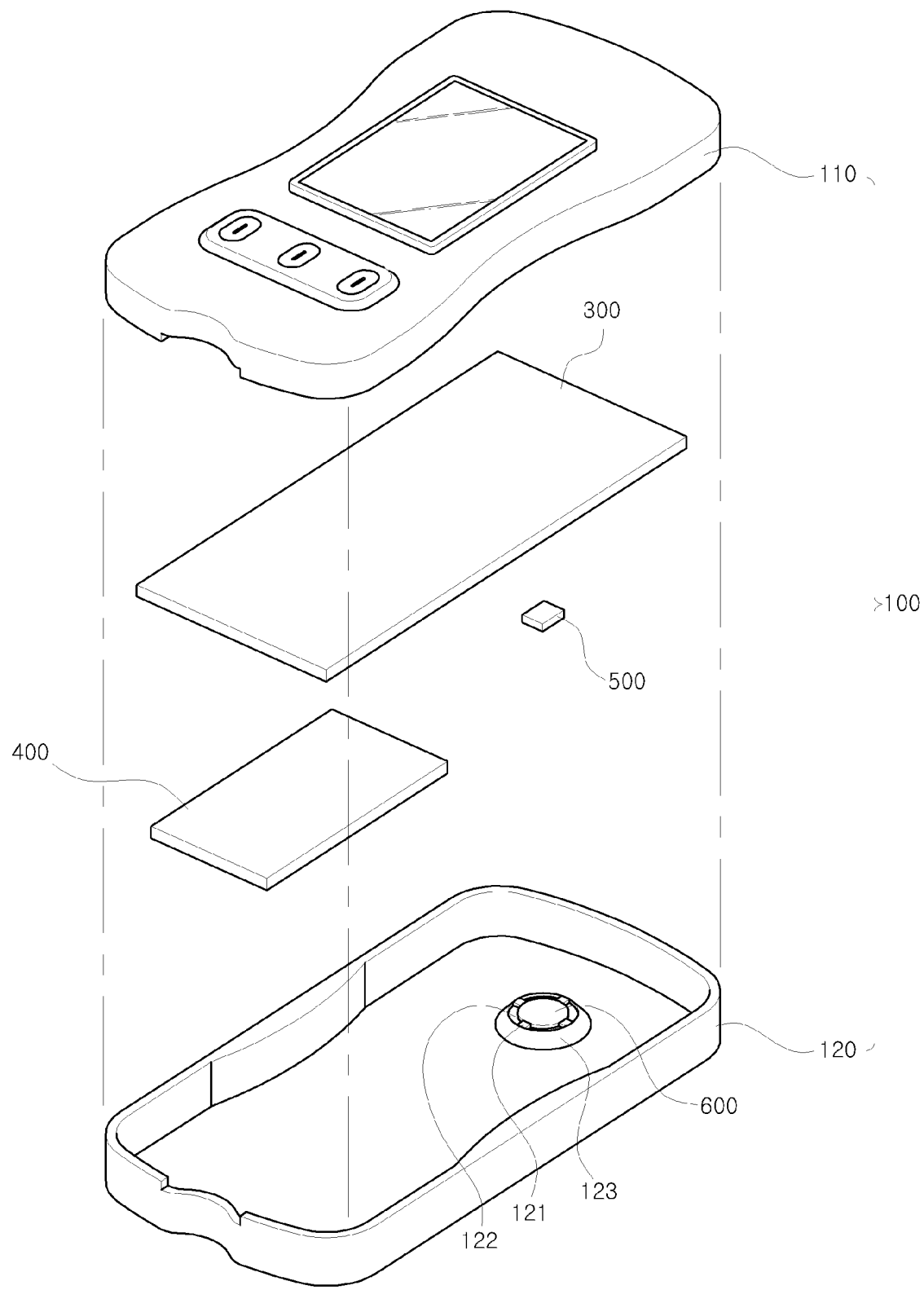
FIG. 2 is an exploded perspective view schematically illustrating the internal structure of the portable blood glucose measuring device according to the embodiment of the present invention.
Figure 3:
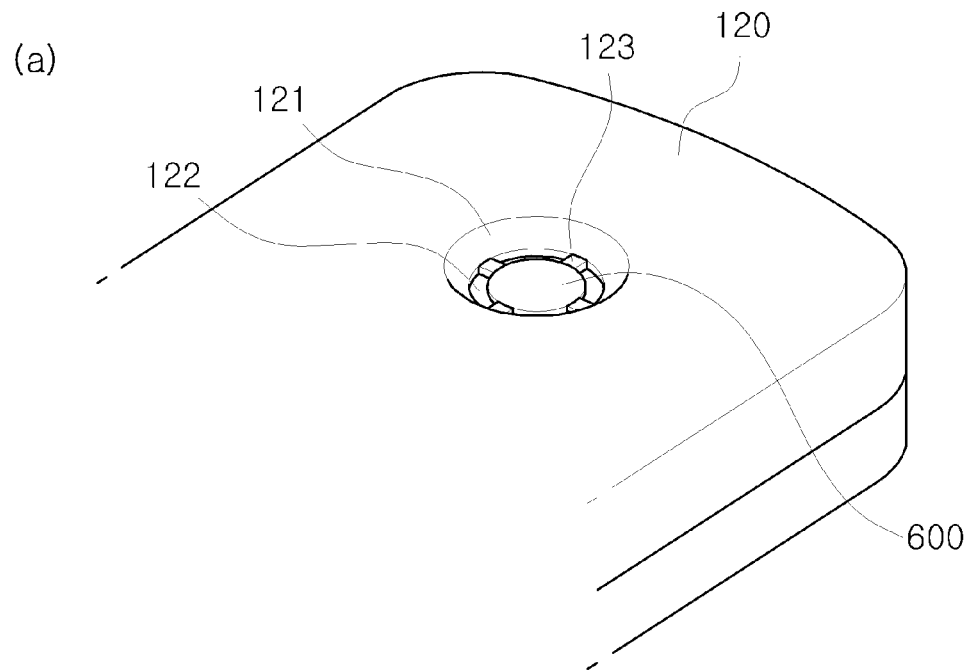
FIG. 3 illustrates exemplary mounting structures of the portable blood glucose measuring device according to embodiments of the present invention, wherein temperature-measuring media are seated in the mounting structures.
Figure 3:
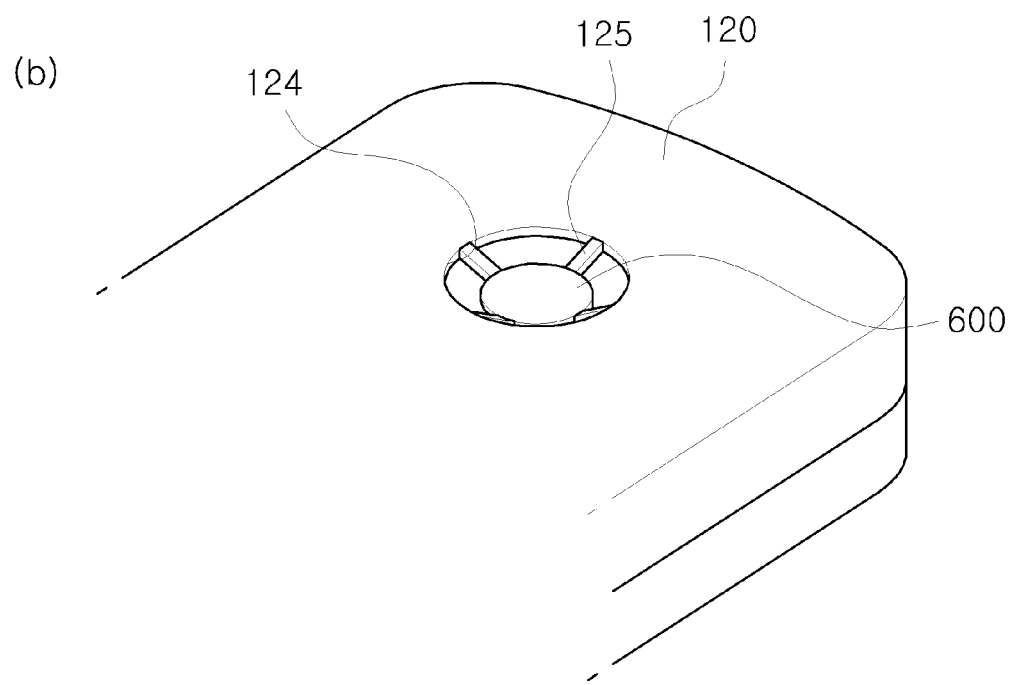
Figure 4:
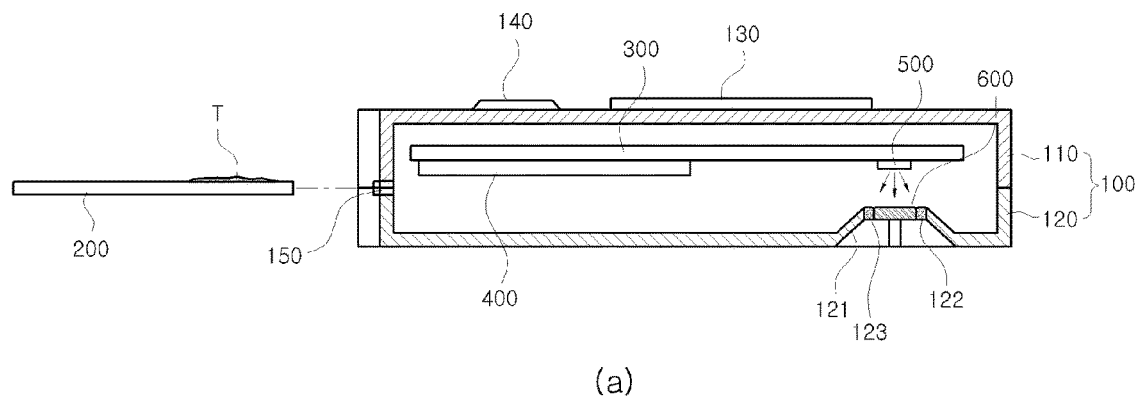
FIG. 4 is cross-sectional views schematically illustrating the internal structures of the portable blood glucose measuring device according to embodiments of the present invention.
Figure 4:
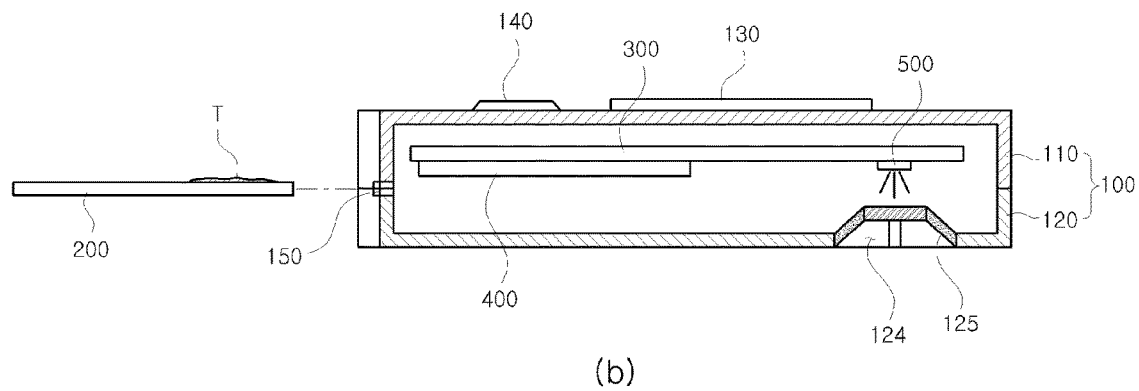

FIG. 1 is a perspective view schematically illustrating the contour of a portable blood glucose measuring device according to an embodiment of the present invention, FIG. 2 is an exploded perspective view schematically illustrating the internal structure of the portable blood glucose measuring device according to the embodiment of the present invention, FIG. 3 illustrates exemplary mounting structures of the portable blood glucose measuring device according to embodiments of the present invention, wherein temperature-measuring media are seated in the mounting structures, and FIG. 4 is cross-sectional views schematically illustrating the internal structures of the portable blood glucose measuring device according to embodiments of the present invention.

The portable blood glucose measuring device according to the embodiment of the present invention is a device able to measure the temperature of an actual measurement environment, thereby improving the accuracy of the result of measurement of a blood glucose level. The portable blood glucose measuring device includes a housing 100, a printed circuit board (PCB) 300, a temperature measuring medium 600, and an infrared (IR) temperature sensor 500.

The housing 100 has an accommodation space defined therein. As illustrated in FIG. 1 and FIG. 2, the housing 100 can be divided into a top housing 110 and a bottom housing 120. The housing 100 has a strip inlet 150 in a side surface, through which a sensor strip 200 can be input to the inner space of the housing 100. As described above in the background art section, a blood sample T is attached to the sensor strip 200. Then, the sensor strip 200 having the blood sample T is input to the strip inlet 150. A control button part 140 and a display part 130 are disposed on the top surface of the housing 100. The control button part 140 allows a user to operate the device, while the display part 130 displays the measured blood glucose level of the blood sample T in a numerical value.

The PCB 300 is disposed within the housing 100, and a blood glucose measuring module 400 is disposed on the PCB 300. The blood glucose measuring module 400 is configured to inspect the blood sample T on the sensor strip 200 input through the strip inlet 150 to measure the blood glucose level of the blood sample T. The blood glucose measuring module 400 calculates the blood glucose level of the blood sample T using a separate calculator and transmits the calculated blood glucose level to the display part 130, so that the blood glucose level is displayed on the display part 130. An application method of calculating the blood glucose level by inspecting the blood sample T is the same as the method of a typical blood glucose measuring device, and a detailed description thereof will be omitted.

The temperature measuring medium 600 functions as an object, the temperature of which is to be measured by the IR temperature sensor 500 that will be described later. The temperature measuring medium 600 is disposed on the housing 100 such that the temperature measuring medium 600 is exposed externally. For example, as illustrated in FIG. 2, the temperature measuring medium 600 may be disposed on the bottom surface of the bottom housing 120.

The IR temperature sensor 500 is disposed within the housing 100, mounted on the PCB 300. The IR temperature sensor 500 is configured to measure the temperature of the above-described temperature measuring medium 600 in a contactless manner.

Thus, in the portable blood glucose measuring device according to the embodiment of the present invention, the temperature measuring medium 600 is disposed on the housing 100 to be exposed externally, such that the temperature of the temperature measuring medium 600 changes rapidly depending on changes in the outside temperature. It is possible to measure the temperature of the temperature measuring medium 600 using the IR temperature sensor 500, thereby more accurately measuring the actual temperature of the outer environment.

Here, the blood glucose measuring module 400 produces the result of measurement of a blood glucose level by considering the temperature measured by the IR temperature sensor 500.

According to this structure, the portable blood glucose measuring device according to the embodiment of the present invention can more accurately measure the outside temperature using the temperature measuring medium 600, the temperature of which rapidly changes depending on the outside temperature, and the IR temperature sensor 500 measuring the temperature of the temperature measuring medium 600, and can produce the result of measurement of a blood glucose level by considering the temperature that has been more accurately measured in this manner, thereby improving the accuracy of the result of measurement of the blood glucose level.

More specifically, as described above in the background art section, a conventional portable blood glucose measuring device fails to appropriately reflect the actual temperature of the surrounding environment, since the temperature of the enclosed inner space is measured using the temperature sensor disposed within the housing. In contrast, according to the present invention, the separate temperature measuring medium 600 is disposed to be exposed externally, such that the temperature thereof rapidly changes depending on changes in the outside temperature, and the IR temperature sensor 500 measures the temperature of the temperature measuring medium 600. It is therefore possible to more accurately measure the actual temperature of the surrounding environment and produce the result of measurement of a blood glucose level by reflecting the measured temperature, thereby improving the accuracy of the result of measurement.

Here, it is preferable that the temperature measuring medium 600 is formed of a material that rapidly changes depending on changes in the outside temperature. For example, the temperature measuring medium 600 may be formed of a metal material having a relatively small specific heat. The material having a small specific heat may be aluminum, copper, or the like.

In addition, it is preferable that the temperature measuring medium 600 has a small volume such that the temperature thereof can easily change. In this regard, as illustrated in FIG. 2 and FIG. 3, the temperature measuring medium 600 may be provided in the shape of a thin plate. It is preferable that the temperature measuring medium 600 has a large area to be in contact with the ambient air to activate heat transfer to the ambient air. Although not shown, the temperature measuring medium 600 may have a plurality of embossed protrusions (not shown) on the externally exposed surface.

As illustrated in FIG. 2, the temperature measuring medium 600 may be disposed on the bottom surface of the housing 100 such that the temperature measuring medium 600 is exposed externally. When the temperature measuring medium 600 is exposed externally as described above, the temperature measuring medium 600 may be brought into contact with a hand of the user or an object, so that heat may be transferred thereto from the hand or the object. Accordingly, it is preferable that the temperature measuring medium 600 is disposed on one surface of the housing 100 and has a concave shape, as illustrated in FIG. 3.

In this regard, as illustrated in parts (a) of FIG. 3 and FIG. 4, the housing 100 has a concave recess 121 formed on one surface thereof, the concave recess 121 being depressed in the direction of the inner space of the housing 100. A through-hole 122 is formed in the bottom of the concave recess 121, such that the temperature measuring medium 600 is fitted into the through-hole 122. The temperature measuring medium 600 can be fitted into the through-hole 122 of the concave recess 121 such that the temperature measuring medium 600 does not protrude from the side surface of the housing 100.

Here, a plurality of fixing protrusions 123 are formed on the inner circumference of the through-hole 122 to be spaced apart from each other in the radial direction, such that heat transfer between the temperature measuring medium 600 and the housing 100 can be minimized. The temperature measuring medium 600 may be fixedly held by the fixing protrusions 123.

With this configuration, the temperature measuring medium 600 and the housing 100 are in contact with each other such that a limited heat contact area is defined therebetween. Accordingly, the low thermal conductivity between the temperature measuring medium 600 and the housing 100 may further facilitate a temperature change due to a change in the outside temperature. In addition, the fixing protrusions 123 may be formed of an insulating material to prevent thermal contact between the temperature measuring medium 600 and the housing 100.

In addition, as illustrated in parts (b) of FIG. 3 and FIG. 4, a through-hole 124 is formed in one surface of the housing 100. Separate fixing rods 125 are disposed on the inner circumference of the through-hole 124 to be inclined downward in the direction of the inner space of the housing 100. The temperature measuring medium 600 may be configured to be fixedly held by the fixing rods 125. Here, the fixing rods 125 may be formed of an insulating material.

The temperature measuring medium 600 may be formed in a variety of other ways to minimize contact with the housing 100. Due to these structures, the temperature of the temperature measuring medium 600 may change by more sensitively reacting with the outside temperature independently of the housing 100. It is possible to more accurately measure the temperature of the surrounding environment by measuring the temperature of the temperature measuring medium 600 using the IR temperature sensor 500. Since a blood glucose level is measured in consideration of the temperature of the surrounding environment, a more accurate result can be obtained in the measurement of the blood glucose level.

The foregoing descriptions have been presented in order to illustrate the certain principles of the present invention. A person skilled in the art to which the invention relates could make many modifications and variations without departing from the principle of the invention. The foregoing embodiments disclosed herein shall be interpreted as illustrative only but not as limitative of the principle and scope of the disclosure. It should be understood that the scope of the invention shall be defined by the appended Claims and all of their equivalents fall within the scope of the disclosure.

The invention claimed is:

1. A portable blood glucose measuring device comprising:
a housing having a strip inlet allowing a sensor strip having a blood sample attached thereto to be input into an inner space of the housing, wherein a through-hole is formed in the housing;
a printed circuit board disposed within the housing, wherein a blood glucose measuring module configured to measure a blood glucose level by inspecting the blood sampled attached to the sensor strip is disposed on the printed circuit board;
a temperature measuring medium disposed at the through-hole formed in the housing; and
an infrared temperature sensor disposed within the housing to measure a temperature of the temperature measuring medium, which is disposed in the housing, exposed outside of the housing through the through-hole formed in the outer surface of the housing, and spaced apart from the infrared temperature sensor, in a contactless manner,
wherein the blood glucose measuring module produces a result of measurement of the blood glucose level.

2. The portable blood glucose measuring device according to claim 1, wherein the temperature measuring medium is made of a material having a relatively small specific heat.

3. The portable blood glucose measuring device according to claim 2, wherein
the housing has a concave recess depressed in a direction of the inner space thereof,
the through-hole is formed in a bottom of the concave recess, allowing the temperature measuring medium to fitted thereinto, and
the temperature measuring medium is fitted into the through-hole, such that the temperature measuring medium does not protrude from a side surface of the housing.

4. The portable blood glucose measuring device according to claim 3, wherein a plurality of fixing protrusions are formed on an inner circumference of the through-hole to be spaced apart from each other in a radial direction, and the temperature measuring medium is fixedly held by the fixing protrusions.

5. The portable blood glucose measuring device according to claim 4, wherein the fixing protrusions are formed of an insulating material.

6. The portable blood glucose measuring device according to claim 2, wherein the temperature measuring medium has a shape of a thin plate.

7. The portable blood glucose measuring device according to claim 6, wherein
the housing has a concave recess depressed in a direction of the inner space thereof,
the through-hole is formed in a bottom of the concave recess, allowing the temperature measuring medium to fitted thereinto, and
the temperature measuring medium is fitted into the through-hole, such that the temperature measuring medium does not protrude from a side surface of the housing.

8. The portable blood glucose measuring device according to claim 7, wherein a plurality of fixing protrusions are formed on an inner circumference of the through-hole to be spaced apart from each other in a radial direction, and the temperature measuring medium is fixedly held by the fixing protrusions.

9. The portable blood glucose measuring device according to claim 8, wherein the fixing protrusions are formed of an insulating material.

10. The portable blood glucose measuring device according to claim 6, wherein the temperature measuring medium comprises a plurality of embossed protrusions formed on an externally exposed surface.

11. The portable blood glucose measuring device according to claim 10, wherein
the housing has a concave recess depressed in a direction of the inner space thereof,
the through-hole is formed in a bottom of the concave recess, allowing the temperature measuring medium to fitted thereinto, and
the temperature measuring medium is fitted into the through-hole, such that the temperature measuring medium does not protrude from a side surface of the housing.

12. The portable blood glucose measuring device according to claim 11, wherein a plurality of fixing protrusions are formed on an inner circumference of the through-hole to be spaced apart from each other in a radial direction, and the temperature measuring medium is fixedly held by the fixing protrusions.

13. The portable blood glucose measuring device according to claim 12, wherein the fixing protrusions are formed of an insulating material.

14. The portable blood glucose measuring device according to claim 1, wherein
the housing has a concave recess depressed in a direction of the inner space thereof,
the through-hole is formed in a bottom of the concave recess, allowing the temperature measuring medium to fitted thereinto, and the temperature measuring medium is fitted into the through-hole, such that the temperature measuring medium does not protrude from a side surface of the housing.

15. The portable blood glucose measuring device according to claim 14, wherein a plurality of fixing protrusions are formed on an inner circumference of the through-hole to be spaced apart from each other in a radial direction, and the temperature measuring medium is fixedly held by the fixing protrusions.

16. The portable blood glucose measuring device according to claim 15, wherein the fixing protrusions are formed of an insulating material.

\* \* \* \* \*